United States Patent [19]

Badertscher

[11] Patent Number: 4,834,896
[45] Date of Patent: May 30, 1989

[54] PHOSPHORIC ACID PARTIAL ESTER COMPOSITIONS AND METHOD OF FATTING LEATHER THEREWITH

[75] Inventor: Markus Badertscher, Birsfelden, Switzerland

[73] Assignee: Sandoz Ltd., Basel, Switzerland

[21] Appl. No.: 127,857

[22] Filed: Dec. 2, 1987

[30] Foreign Application Priority Data

Dec. 4, 1986 [DE] Fed. Rep. of Germany ....... 3641402
Sep. 3, 1987 [DE] Fed. Rep. of Germany ....... 3729396

[51] Int. Cl.$^4$ ........................... C14C 9/02; B01F 17/14
[52] U.S. Cl. .................................. 252/8.57; 8/94.33; 427/337; 427/389; 427/412; 428/473
[58] Field of Search ............... 252/8.57; 427/337, 389, 427/412; 428/473; 8/94.33

[56] References Cited

FOREIGN PATENT DOCUMENTS 2154605 9/1985 United Kingdom .

Primary Examiner—Paul Lieberman
Assistant Examiner—John F. McNally
Attorney, Agent, or Firm—Gerald D. Sharkin; Richard E. Vila; Thomas C. Doyle

[57] ABSTRACT

Compositions comprising
 (a) phosphoric acid partial esters of oxyalkylated $C_{14-20}$-fatty alcohols and
 (b) phosphoric acid partial esters of non-oxyalkylated $C_{12-20}$-fatty alcohols
optionally together with
 (c) a hydrophilic non-ionic or anionic surfactant different from (a) a (b)
 but essentially free of optionally chemically modified natural leather-fatting agents
are excellently suitable for the softening and fatting of leather without admixture of optionally chemically modified natural leather fatting agents.

41 Claims, No Drawings

PHOSPHORIC ACID PARTIAL ESTER COMPOSITIONS AND METHOD OF FATTING LEATHER THEREWITH

From GB 2 105 745 A and 2 163 451 A it is known to use phosphoric acid partial esters of particular oxyalkylated fatty alcohols as fatting agents for leather. From GB 2 154 605 A it is known to fat-liquor leather with compositions containing phosphoric acid partial esters of particular oxyalkylated fatty alcohols together with natural, optionally chemically modified, leather-fatting agents. From GB 2 154 605 A it is also known to use compositions containing phosphoric acid partial esters of particular oxyalkylated fatty alcohols and phosphoric acid partial esters of particular non-oxyalkylated fatty alcohols together with natural leather-fatting agents or chemically modified natural leather-fatting agents for the fatting of leather. It has now been found that compositions comprising phosphoric acid partial esters of particular oxyalkylated fatty alcohols together with phosphoric acid partial esters of particular non-oxyalkylated fatty alcohols without any admixture of other fatting agents, in particular without and admixture of natural or chemically modified natural fatting agents are surprisingly eminently suitable for the softening and fatting of tanned leather substrates, i.e. in particular in order to achieve an excellent soft and silky handle.

The invention relates to the defined softening fatting method with the defined phosphoric acid partial ester compositions without any admixture of other fatting agents and to the corresponding phosphoric acid partial ester compositions which are essentially free of other fatting agents.

Accordingly, the invention provides a composition comprising (a) a phosphoric acid partial ester of an oxyalkylated $C_{14-20}$-fatty alcohol or a mixture of such partial esters and (b) a phosphoric acid partial ester of a non-oxyalkylated $C_{12-20}$-fatty alcohol or a mixture of such phosphoric acid partial esters, in free acid or salt form, which is essentially free of any natural leather fatting agent and of any chemically modified natural leather fatting agent.

The oxyalkylated $C_{14-20}$-fatty alcohols in component (a) are preferably addition products of 2–10, preferably 2–6 moles of alkylene oxide to 1 mole of fatty alcohol, alkylene signifying ethylene-1,2 and optionally propylene-1,2. Preferably at least some of the alkyleneoxy units are ethyleneoxy. More preferably all of the alkyleneoxy units are ethyleneoxy. More preferably in component (a) 2–6 ethyleneoxy units, in particular 3–5 ethyleneoxy units are present per fatty alcohol radical. The higher aliphatic fatty alcohols to which the alkyleneoxy units are added may be unsaturated or preferably saturated, more preferably primary alcohols, containing 14–20 carbon atoms; n-alkenols and in particular n-alkanols being preferred. The following primary alkanols and alkenols are worth mention: tetradecanol, cetyl alcohol, oleyl alcohol and stearyl alcohol and technical mixtures containing such alcohols or consisting thereof, e.g. tallow fatty alcohol. The alcohols with 16–18 carbon atoms and tallow fatty alcohol are particularly preferred. Most preferred are the oxyethylation products of cetyl alcohol, stearyl alcohol, oleyl alcohol and tallow fatty alcohol with 3–5 ethyleneoxide units per fatty alcohol radical.

These addition products are obtainable in a manner known per se, e.g. by reaction of alcohols with alkyleneoxides in the presence of catalytic quantities of an alkali metal hydroxide at elevated temperature or also according to other known methods.

The non-oxyalkylated fatty alcohols of component (b) contain preferably 12–16, more preferably 12–15 carbon atoms. The fatty alcohols may advantageously be linear or branched primary or also secondary alcohols and may be unitary alcohols or mixtures in particular technical mixtures. If they are mixtures the above indicated number of carbon atoms represents the average number. Particularly preferred alcohols are lauryl alcohol and alcohol mixtures containing preponderantly $C_{12}$- to $C_{15}$-alcohols—e.g. $C_{13-15}$-alkanols—preferably wherein $C_{12-14}$-alcohols, in particular dodecanol, prevail. Particularly preferred are alcohols that contain 12–13.8 carbon atoms on the average. The following alcohols are worth mention as alcohols for (b): the ones mentioned above for (a) and further lauryl alcohol, coconut fatty alcohol, palm kernel alcohol and further technical alkanols that contain preponderantly $C_{12-15}$-alkanols, in particular technical tetradecanol (which is essentially a mixture of tri-, tetra- and pentadecanol) and technical tridecanol (which is essentially a mixture of $C_{12-15}$-alkanols).

The phosphoric acid partial esters (a) and (b) may be in the form of the free acids or in salt form, preferably they are at least in part in the form of their salts. They may be produced according to known methods, e.g. by reaction of the $C_{12-20}$-fatty alcohols, or of the polyalkylene glycol monoethers of the $C_{14-20}$-fatty alcohols with phosphorus pentoxide, phosphorus oxychloride or polyphosphoric acid at elevated temperature. After the reaction the partial esters may, if desired, be reacted with a base to give the corresponding salts forms. The cations for the salt formation may be alkali metal cations (particularly lithium, sodium and potassium, preferably sodium and potassium) and ammonium, the ammonium may be substituted or unsubstituted; the substituted ammonium may be substituted by alkyl with 1–2 carbon atoms and/or alkanol with 2–3 carbon atoms and may be e.g. mono-, di- and trialkylammonium, mono-, di- and trialkanolammonium and alkylated mono- or dialkanolammonium, preferably mono-, di- and trimethylammonium, mono-, di- and triethylammonium, mono-, di- and triisopropanolammonium, mono-, di- and triethanolammonium and methylethanolammonium. For salt formation from the partial ester the above cations may be added as aqueous solutions of the corresponding hydroxides or for alkali metals also as the corresponding salts of weak acids (e.g. as alkali metal carbonates or bicarbonates); for the production of amine salts the corresponding amines may be added as aqueous solutions or preferably in water-free form.

The obtained phosphoric acid partial esters, in particular the preferred ones, may be represented by the following formulae

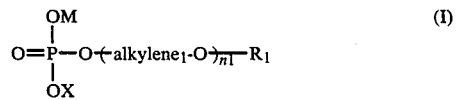

and

-continued

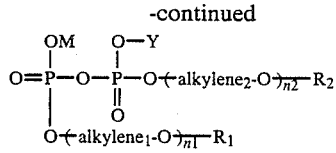

wherein
M signifies hydrogen, alkali metal or ammonium,
X and Y signify M or $-(\text{alkylene}_3-O)_{\overline{n3}}R_3$,
$R_1$, $R_2$ and $R_3$ independently from each other signify $C_{14-20}$-alkyl or -alkenyl for component (a), or $C_{12-20}$-alkyl or -alkenyl for component (b),
$\text{alkylene}_1$, $\text{alkylene}_2$ and $\text{alkylene}_3$ independently from each other signifiy ethylene-1,2 or propylene-1,2
and $n_1$, $n_2$ and $n_3$ independently from each other are zero for the component (b), or each on the average is a number from 2 to 10 for component (a)

the various alkyleneoxy units in (a) being the same or different, preferably at least some of them being ethylenoxy. If more then one alkyl or alkenyl radical $R_1$ and $R_2$ resp. $R_3$ are present they may be the same or different.

In the above formulae the indices $n_1$, $n_2$ and $n_3$ represent average values of the number of added alkylene oxide units to the respective alcohols; also the radicals $R_1$, $R_2$ and $R_3$ may correspond to average significances if the starting alcohol is not a single component but e.g. a technical mixture of alcohols. Formula (II) represents compounds that may exist practically only in a water-free or nearly water-free medium, since in the presence of water they are hydrolysed to compounds of formula (I). In formula (II) M is preferably hydrogen and if Y signifies M this is also preferably hydrogen. If the above partial esters are dibasic monoesters, as the compounds of formula (I) in which X is M, then, preferably only one of the two hydroxy groups is neutralised, so that one of the two symbols M means hydrogen and the other means a cation as indicated above (preferably alkali metal or ammonium). For the production of the salt forms, the phosphoric acid partial esters are preferably reacted with the corresponding base, up to a pH of preferably 5 to 8, more preferably 6 to 8 (measured on their 3.5% aqueous solution).

The weight ratio of component (b) to component (a) is preferably in the range of 1:0.2 to 1:0.8, preferably 1:0.3 to 1:0.6.

In the compositions of the invention (a) and (b) are preferably mixed with a hydrophilic surfactant (c) which is non-ionic surfactant or an anionic surfactant which is different from (a) and (b). The further anionic and non-ionic surfactants may be advantageously one or more of the following:

(1) Addition products of 1 to 100 moles of ethylene oxide to one mole of $C_{4-24}$-alcohols, phenol or mono- or di-($C_{1-12}$-alkyl)phenols; preferably addition products of 10-100 moles of ethylene oxide to one mole of aliphatic $C_{6-22}$-, preferably $C_{12-22}$-alcohols, in particular saturated alcohols, e.g. tetramethylnonyl alcohol, lauryl alcohol, myristyl alcohol, cetyl alcohol, stearyl alcohol, arachidyl alcohol or behenyl alcohol and unsaturated alcohols for example oleyl alcohol; particularly preferred are addition products of 20-80 ethylene oxide units to these alcohols; further addition products of 2-50 moles ethylene oxide to one mole ($C_{3-9}$-alkyl)$_{1-2}$-phenol.

(2) Carboxymethyl derivatives of the non-ionic surfactants mentioned under (1), i.e. e.g. their reaction products with chloracetic acid.

(3) Sulphation products of the non-ionic surfactants described under (1) of the formula

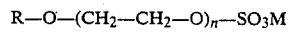

wherein R signifies the hydrocarbon radical of the alcohol or phenol mentioned under (1), n being preferably 1-25 and M hydrogen or a cation as mentioned above.

(4) Alkylbenzene sulphonates and paraffin sulphonates.

Advantageously at least some of the surfactants have O/W-emulsifier character or in particular protective colloid character.

The anionic surfactants may also be employed in the form of the corresponding salts wherein the cations may be as indicated above for the phosphoric acid partial esters.

Of the above surfactants the non-ionic ones, in particular the ones indicated under (1) are preferred, the aliphatic higher molecular weight derivatives being more preferred.

Component (c) is employed advantageously in small quantities, in particular in quantities that represent only a fraction of the total quantity of (a)+(b). For 100 parts by weight of the mixture of (a) and (b) there are employed preferably 0.8 to 12, more preferably 3 to 9 parts by weight of component (c).

The mixtures of (a) and (b) and preferably also (c) as defined above are preferably formulated together with water to aqueous concentrated compositions and thus the invention further provides aqueous compositions (in particular aqueous solutions or dispersions) that contain the components (a), (b) and preferably also (c) and are essentially free of natural and chemically modified natural leather-fatting agents. In particular the aqueous composition of the invention consist only of the above defined components (a), (b) and preferably also (c) and water, plus optionally a base, components (a) and (b) being preferably in part or totally neutralised with one or more bases.

The aqueous compositions of the invention may be produced in known manner suitably by admixing the components (a), (b) and preferably also (c) if necessary heating to melt the components and adding water (if necessary with agitation); a compound for the adjustment of the pH-value may be added before or after the addition of water.

The pH-value of the aqueous composition is advantageously in the range of from 3.5 to 10, preferably from 5 to 9, more preferably from 6.5 to 8 (measured on an aqueous composition containing 4.5% dry substance) and may be adjusted by addition of known bases, especially as suitable for the formation of the above-mentioned salts of the phosphoric acid partial esters (e.g. alkali metal hydroxide solution, ammonia or amines).

If desired, preserving agents, e.g. a fungicide, may be added to the composition.

The dry substance content of the aqueous composition of the invention is preferably in the range of 10 to 65%, more preferably 30 to 60% (with respect to the total weight of the dispersion). If desired or necessary, they may be diluted before they are used for the treatment of leather.

The above described compositions serve as leather fatting agents and thus the invention further provides a method of fatting leather substrates with these compositions. In particular, the invention provides a process for fatting tanned leathers and pelts, wherein the leather or pelt is fatted in aqueous medium with a composition as described above, without any admixture of optionally chemically modified natural leather-fatting agents.

Any kind of leather and pelt that has been tanned by any usual tanning method, in particular vegetable, mineral, synthetic or combined tanned (e.g. chrome-tanned, zirconyl-tanned or aluminium-tanned) or also correspondingly re-tanned and as, in general, employed as a substrate for known fatting methods, may be treated with the compositions of the invention and by the method of the invention. The following preferred kinds of leather may be mentioned: grain leather e.g. nappa from sheep, goat or cow, boxleather from calf or cow, sueded leather, e.g. velours from sheep, goat or calf and hunting leather, split velours from cow- or calf-skin and nubuk-leather, further also fur-bearing sueded leather and furs for clothing.

Optionally, the substrate may have been dyed in a separate dye bath before the fatting treatment or the fatting treatment may be carried out subsequent to the dyeing step in the same aqueous medium from which the substrate has been dyed.

The fatting according to the invention is carried out, preferably from aqueous medium, without admixture of any natural and/or chemically modified natural leather-fatting agents, in particular in the absence thereof, preferably in the absence of any further fatting agents. If desired, the leather substrate may have been otherwise fatted before the fatting of the invention; preferably, however, the leather is not treated with any other fatting agents.

The fatting of the leather or pelts according to the invention may be carried out in conventional manner, suitably by exhaustion. The concentration of all of the phosphoric acid partial esters (a)+(b) is preferably within the range of 0.2-15%, more preferably 2-8% by weight with respect to the wet-weight of the leather; the aqueous treatment-liquors are preferably from slightly alkaline to clearly acid (particularly pH 2-9), preferably the liquor is neutral to slightly acid (pH 4-7). The fatting with these aqueous liquors is carried out preferably in the termperature range between 20° and 70° C., more preferably between 40° and 60° C. The pH may be suitably adjusted with known acids, bases and/or buffers, preferably with formic acid, ammonium carbonate or alkali metal carbonate.

Upon treatment with the described fatting compositions the substrates may, if desired, be after-treated with polyvalent metal or metal oxy cations. The polyvalent cations for the after-treatment are preferably magnesium, calicum, barium, aluminium, chromium-(III) and zirconyl of which aluminium, chromium-(III) and zirconyl are preferred. The after-treatment is suitably carried out by addition of corresponding compounds of the polyvalent metals, in particular of their oxides, hydroxides and/or salts of the aqueous treatment liquor, the hydrosoluble salts being preferred, in particular aluminium sulfate, potassium alum, chromium-(III)-sulfate, potassium chromium alum, chromium hydroxy sulfate, zirconyl-chloride, zirconyl-sulfate and zirconyl-acetate.

The concentration of the above-mentioned after-treatment compounds, calculated as metal cations, with respect to the dry weight of the phosphoric acid partial ester is preferably in the range of from 1-100%, more preferably 5-20%. The after-treatment is preferably carried out by exhaustion from aqueous medium. It may advantageously be carried out by exhaustion from the same aqueous medium as that in which the fatting step was carried out, just after the fatting procedure (optionaly with an intermediate dyeing step also in the same aqueous medium). The polyvalent metal compound for the after-treatment is advantageously added only after the build-up of the fatting agent on the substrate is practically complete. The after-treatment is preferably carried out at temperatures between 20° and 70° C., more preferably between 40° and 60° C., preferably under slightly alkaline to clearly acidic conditions (in particular pH 2-9), more preferably under neutral to slightly acidic conditions (in particular pH 4-7). On completion of the after-treatment with the polyvalent cations the leather and pelts may be finished by known methods.

Preferably the leather is, however, not after-treated with the polyvalent metal or metal oxy cations.

By the fatting process of the invention, there are obtained optimally fatted leathers and pelts of an excellently soft and silky handle— grain leather having a particularly pleasant waxy and silky grain—and which further exhibit notable tear-resistance and suppleness as well as the general fastnesses that are usually required for leather. By the after-treatment with the mentioned polyvalent metal cations, there may be further achieved an improved hydrophobising effect. The obtained fatting is further highly resistant to the solvents usually employed in the dry cleaning.

The following examples illustrate the invention. The percentages are by weight and the temperatures are indicated in degrees Celsius. In the application examples the percentages refer to the wet weight of the substrates, if there is not unequivocally intended the concentration of a solution or dispersion. The indicated dilutions are by volume with water.

EXAMPLE 1

In a glass or steel beaker 20 g of the oxyethylation products of 1 mole of oleyl alcohol with 60 moles of ethylene oxide, 100 g of the phosphoric acid partial ester of formula (I) in which $R_1$ is tallow alkyl, $n_1$ is 3.8, alkylene$_1$ is ethylene, X is hydrogen and M is hydrogen and 265 g of the phosphoric acid partial ester of formula (I) in which $R_1$ is technical tetradecyl (technical mixture of tridecyl, tetradecyl and pentadecyl), $n_1$ is zero, M is hydrogen and X is by 50 mol% hydrogen and by 50 mol% technical tetradecyl are melted at a temperature of 70°-75° C. and mixed until the melt appears clear and homogeneous. At this point 65 g of a 30% sodium hydroxide solution are added slowly while stirring with the anchor stirrer. Then 550 g of demineralized water of 20° C. are added slowly and with good stirring of the mixture. At the beginning there is formed a W/O-emulsion, which then converts to an O/W-emulsion. The phase inversion starts when about 30% of the quantity of water have been added. The obtained dispersion is milky and opalescing. The dispersed particles have a particle size $\leq 3$ μm, the main amount having a particle size $<1$ μm. The pH of a 1+9 dilution with demineralized water is 7,0 to 7,5.

EXAMPLE 2

Example 1 is repeated with the difference that in place of the phosphoric acid partial ester of technical tetradecanol the analogous phosphoric acid partial ester of lauryl alcohol is employed.

EXAMPLE 3

Example 1 is repeated with the difference that in place of the phosphoric acid partial ester of the technical tetradecanol the analogous ester of coconut fatty alcohol is employed.

EXAMPLE 4

Example 1 is repeated with the difference that in place of the phosphoric acid partial ester of technical tetradecanol the analogous ester of technical tridecanol (mixture of $C_{12-15}$-alcohols) is employed.

APPLICATION EXAMPLE A1

Production of shoe upper leather

Material: chrome-tanned cow-hides (wet blue) of a thickness of 1.5 mm.

The leather is washed in a retanning vessel with 200% of water at 35° C. for 10 minutes, then the liquor is drained off and 100% of water at 35° C., 1% of sodium formate and 0,5% of sodium bicarbonate are added and the treatment is continued for 40 minutes. The pH of the liquor is between 4,5 and 5,0. In the same bath the leather is retanned with 4% of polyacrylic acid during 40 minutes, then with 4% of syntan (condensation product of aromatic sulphone, aromatic sulphonic acid and formaldehyde) and 2% of dimethylolethylene urea for a further 40 minutes. Then the liquor is drained off and the leather is washed in a fresh liquor of 200% of water at 50° C. for 10 minutes, which again is drained off. The leather is then dyed in a fresh liquor of 100% of water at 55° C. with 0,8% C.I. Acid Brown 359 during 30 minutes; 8–10% of the dispersion of Example 1 are added and the treatment of the leather with this liquor is continued for 90–120 minutes. The liquor is then acidified with 1% of formic acid of 85% concentration (diluted 1:5). After 20 minutes of this treatment, the fatting agents mixture is practically completely exhausted. The liquor is drained off and the treated leather is washed with 200% of water of normal temperature for 10 minutes. Then the bath is drained off, the leather discharged, dried and mechanically finished.

There is obtained an excellently soft leather with a very pleasant silky and waxy handle.

APPLICATION EXAMPLES A2, A3 AND A4

Application Example A1 is repeated, with the difference, that in place of the dispersion of Example 1 the dispersions of Examples 2, 3 and 4 resp. are employed.

APPLICATION EXAMPLE B1

Production of shoe upper leather

Material: chrome-tanned veal hide (wet-blue) of a thickness of 0.9 to 1 mm.

The leather is washed in a retanning vessel with 200% of water at 40° C. for 10 minutes, then the liquor is drained off and 200% of water at 35° C., 1% sodium formate, 0,5% of sodium sulfite and 6% of proteine hydrolysis product are added and the treatment is continued for 60 minutes. The pH of the bath is between 4,5 and 5,0. In the same bath the leather is retanned and pre-fatted with 4% of polyacrylic acid and 3% of the dispersion of example 1 during 40 minutes. Upon addition of 3% of dimethylolethyleneurea the treatment is continued for further 30 minutes. The liquor is then drained off and the leather is washed with 200% of water of 50° C. for 10 minutes. Then the liquor is drained off. 200% of water of 50° C. and 0,5% of the addition product of 105 moles of ethylene oxide to 1 mole of fatty amino propylamine (fatty radical=mixture of behenyl and arachidyl) are added and after 5 minutes 1,2% of C.I. Acid Brown 432 are added and the treatment is continued for 30 minutes. Then 10% of the dispersion of example 1 are added (as main fatting) and the treatment is continued for 60 minutes. The liquor is then acidified with 1% of 85% strength formic acid (diluted 1:5); after 20 minutes of this treatment the liquor is drained off and the leather is washed with 200% of water of normal temperature for 10 minutes, then the bath is drained off, the leather discharged, drained, dryed and mechanically finished. There is obtained an excellently soft leather with very pleasant silky and waxy handle.

APPLICATION EXAMPLES B2, B3 AND B4

The procedure of Application Example B1 is repeated, with the difference that the dispersions of Examples 2, 3 and 4 resp. are employed in place of the dispersion of Example 1.

I claim:

1. A composition comprising
   (a) a phosphoric acid partial ester of an oxyalkylated $C_{14-20}$-fatty alcohol or a mixture thereof and
   (b) a phosphoric acid partial ester of a non-oxyalkylated fatty alcohol selected from the group consisting of lauryl alcohol and alcohol mixtures containing preponderantly $C_{12}$ to $C_{15}$ alcohols
   in free acid or salt form
   and which is essentially free of natural leather fatting agents and chemically modified natural leather fatting agents.

2. A composition according to claim 1 wherein the oxyalkylated fatty alcohols of the esters (a) are addition products of 2–10 moles of ethylene oxide to 1 mole of $C_{14-20}$-fatty alcohol.

3. A composition according to claim 1 wherein the non-oxyalkylated fatty alcohol in (b) is a $C_{12-16}$-alcohol or a technical mixture comprising $C_{12-16}$ alcohols.

4. A composition according to claim 1 further comprising
   (c) a hydrophilic non-ionic surfactant or a hydrophilic anionic surfactant which is different from (a) and (b).

5. A composition according to claim 4 wherein (c) is a non-ionic surfactant which is the addition product of 10–100 moles of ethylene oxide to 1 mole of a $C_{12-22}$-fatty alcohol or a mixture thereof.

6. A composition according to claim 1, wherein (a) and (b) are in the form of their alkali metal salts or ammonium salts or both, alkali metal and ammonium salts.

7. A composition according to claim 1, in the form of an aqueous solution or dispersion.

8. A composition according to claim 4 in the form of an aqueous solution or dispersion.

9. An aqueous composition according to claim 7 with a dry substance content of 10–65%, referred to the total weight of the composition.

10. An aqueous composition according to claim 8 with a dry substrate content of 30-60% referred to the total weight of the composition.

11. A composition according to claim 1, wherein the weight ratio (b):(a) is in the range of 1:0.2 to 1:0.8.

12. A composition according to claim 4, wherein the weight ratio [(a)+(b)]:(c) is in the range of 100:0.8 to 100:12.5 and the weight ratio (b):(a) is in the range of 1:0.2 to 1:0.8.

13. A process for fatting a tanned leather or pelt substrate which comprises applying to the substrate, as the fatting agent, a composition according to claim 1 without any admixture of a natural leather-fatting agent or a chemically modified natural leather-fatting agent.

14. A process according to claim 13 wherein after the fatting the leather or pelt is after-treated with a polyvalent metal or metal oxy cation.

15. Tanned leather or pelt substrate treated by a process according to claim 13.

16. Tanned leather or pelt substrate treated by a process according to claim 13.

17. A composition according to claim 1 wherein (b) is a phosphoric acid partial ester of a non-oxyalkylated fatty alcohol selected from the group consisting of lauryl alcohol and alcohol mixtures in which $C_{12-14}$ alcohols prevail.

18. A composition according to claim 1 wherein (b) is a phosphoric acid ester of a non-oxyalkylated fatty alcohol containing an average of 12-13.8 carbon atoms.

19. A composition according to claim 1 wherein (b) is a phosphoric acid ester of lauryl alcohol, technical tetradecanol, technical tridecanol or coconut fatty alcohol.

20. A composition according to claim 17 wherein the weight ratio (b):(a) is in the range 1:0.2 to 1:0.8.

21. A composition according to claim 17 which further comprises (c) a non-ionic surfactant which is an addition product of 1 to 100 moles of ethylene oxide to one mole of a member of the group consisting of $C_{4-24}$ alcohols, phenol and mono- and di-($C_{1-12}$ alkyl) phenols.

22. A composition according to claim 18 wherein the weight ratio (b):(a) is in the range 1:0.2 to 1:0.8.

23. A composition according to claim 18 which further comprises (c) a non-ionic surfactant which is the addition product of 10-100 moles of ethylene oxide to 1 mole of a $C_{12-22}$ fatty alcohol or a mixture thereof.

24. A composition according to claim 21 wherein the weight ratio ((a)+(b)):(c) is in the range 100:0.8 to 100:12.5 and the weight ratio (b):(a) is in the range of 1:0.2 to 1:0.8.

25. A composition according to claim 23 wherein the weight ratio ((a)+(b)):(c) is in the range 100:0.8 to 100:12.5 and the weight ratio (b):(a) is in the range of 1:0.2 to 1:0.8.

26. A process for fatting a tanned leather or pelt substrate which comprises applying to the substrate, as the fatting agent, from an aqueous medium, a composition according to claim 4 without any admixture of a natural leather fatting agent or a chemically modified natural leather fatting agent.

27. A process for fatting a tanned leather or pelt substrate which comprises applying to the substrate, as the fatting agent, a composition according to claim 18 without any admixture of a natural leather-fatting agent or a chemically modified natural leather-fatting agent.

28. A process for fatting a tanned leather or pelt substrate which comprises applying to the substrate, as the fatting agent, a composition according to claim 20 without any admixture of a natural leather-fatting agent or a chemically modified natural leather-fatting agent.

29. A process for fatting a tanned leather or pelt substrate which comprises applying to the substrate, as the fatting agent, a composition according to claim 25 without any admixture of a natural leather-fatting agent or a chemically modified natural leather-fatting agent.

30. A process according to claim 13 wherein the fatting agent is applied from an aqueous medium in which the concentration of said fatting agent is 0.2 to 15% based on the wet weight of the leather.

31. A process according to claim 27 wherein the fatting agent is applied from an aqueous medium in which the concentration of said fatting agent is 0.2 to 15% based on the wet weight of the leather.

32. A process according to claim 29 wherein the fatting agent is applied from an aqueous medium in which the concentration of said fatting agent is 0.2 to 15% based on the wet weight of the leather.

33. A process for fatting a tanned leather or pelt substrate which comprises applying to the substrate, as fatting agent, a composition comprising
  (a) a phosphoric acid partial ester of an oxyalkylated $C_{14-20}$ fatty alcohol or a mixture thereof and
  (b) a phosphoric acid partial ester of a non-oxyalkylated $C_{12-20}$ fatty alcohol or a mixture thereof, in free acid or salt form,
in the absence of any natural leather fatting agent or chemically modified natural leather fatting agent.

34. A process according to claim 33 in which the fatting agent composition further comprises (c) a hydrophilic non-ionic surfactant or a hydrophilic anionic surfactant which is different from (a) and (b).

35. A process according to claim 33 wherein after the fatting the substrate is after-treated with a polyvalent metal or metal oxy cation.

36. A composition according to claim 1 wherein component (a) is a phosphoric acid partial ester of an oxyalkylated $C_{16-18}$ alcohol or of oxyalkylated tallow fatty alcohol.

37. A composition according to claim 17 wherein component (a) is a phosphoric acid partial ester of an oxyalkylated $C_{16-18}$ alcohol or of oxyalkylated tallow fatty alcohol.

38. A composition according to claim 18 wherein component (a) is a phosphoric acid partial ester of an oxyalkylated $C_{16-18}$ alcohol or of oxyalkylated tallow fatty alcohol.

39. A composition according to claim 18 wherein component (a) is a phosphoric acid partial ester of a product of oxyethylating cetyl, stearyl or oleyl alcohol or tallow fatty alcohol with 3 to 5 mols of ethylene oxide per mole of alcohol.

40. A process according to claim 33 wherein the fatting agent is applied from an aqueous medium in which the concentration of said fatting agent is 0.2 to 15% based on the wet weight of the leather.

41. A tanned leather or pelt substrate treated by a process according to claim 33.

* * * * *